US005588556A

United States Patent [19]

Sancoff et al.

[11] Patent Number: 5,588,556
[45] Date of Patent: Dec. 31, 1996

[54] METHOD FOR GENERATING GAS TO DELIVER LIQUID FROM A CONTAINER

[75] Inventors: Gregory E. Sancoff, Rancho Santa Fe; Mark C. Doyle, San Diego; Frederic P. Field, Solana Beach, all of Calif.

[73] Assignee: River Medical, Inc., San Diego, Calif.

[21] Appl. No.: 461,871

[22] Filed: Jun. 5, 1995

Related U.S. Application Data

[60] Division of Ser. No. 205,875, Mar. 3, 1994, Pat. No. 5,398,850, and a continuation-in-part of Ser. No. 105,327, Aug. 6, 1993, Pat. No. 5,398,851, and Ser. No. 105,284, Aug. 6, 1993, Pat. No. 5,397,303.

[51] Int. Cl.$^6$ ........................................... B65D 83/14
[52] U.S. Cl. .............................. 222/1; 222/394; 222/396
[58] Field of Search ........................... 222/1, 386, 386.5, 222/394, 396, 397, 399, 389; 604/145; 239/322, 323; 169/33, 85; 424/44; 422/305

[56] References Cited

U.S. PATENT DOCUMENTS

| | | | |
|---|---|---|---|
| 524,377 | 8/1894 | Carr | 169/83 |
| 754,037 | 3/1909 | Anderson | 169/75 |
| 1,469,501 | 10/1923 | Dollin | 169/73 |
| 1,731,767 | 10/1929 | Cramer | 222/386.5 |
| 1,832,817 | 11/1931 | Pearsons | 169/80 |
| 2,105,690 | 1/1938 | Greenblatt | 424/44 X |
| 2,312,381 | 3/1943 | Bickenheuser | 424/44 X |
| 2,381,749 | 8/1945 | Hull et al. | 169/81 |
| 2,473,912 | 6/1949 | Schwinn | 137/853 |
| 2,759,337 | 8/1956 | Katz | 252/67 U X |
| 2,815,152 | 12/1957 | Mills | 222/386.5 |
| 2,845,090 | 7/1958 | Rost | 137/853 |
| 2,912,018 | 11/1959 | Leech | 222/399 X |
| 3,023,750 | 3/1962 | Baron | 222/386.5 X |
| 3,053,422 | 9/1962 | Tenison et al. | 222/399 |
| 3,096,000 | 7/1963 | Staley | 222/386.5 X |
| 3,122,181 | 2/1964 | Hebenstreit et al. | 422/305 X |
| 3,146,169 | 8/1964 | Stephenson et al. | 424/467 |
| 3,153,414 | 10/1964 | Beall et al. | 604/142 X |
| 3,175,558 | 3/1965 | Caillouette et al. | 126/204 X |
| 3,178,075 | 4/1965 | Riedel et al. | 222/386.5 |
| 3,217,947 | 11/1965 | Bauerlein | 222/397 |
| 3,357,601 | 12/1967 | Crawford et al. | 222/399 |
| 3,367,545 | 2/1968 | Cook | 222/389 |
| 3,384,113 | 5/1968 | Pennisi | 137/853 |
| 3,385,481 | 5/1968 | Frangos | 222/396 |
| 3,405,845 | 10/1968 | Cook et al. | 222/389 X |
| 3,429,627 | 2/1969 | Young | 126/263.1 X |
| 3,468,308 | 9/1969 | Bierman | 604/132 X |
| 3,577,512 | 5/1971 | Shepherd et al. | 424/471 |
| 3,585,982 | 6/1971 | Hollinshead | 126/263.1 |
| 3,595,467 | 7/1971 | Goglio | 222/396 |
| 3,640,277 | 2/1972 | Adelberg | 222/386.5 X |
| 3,667,652 | 6/1972 | Morane et al. | 222/386 |
| 3,708,089 | 1/1973 | Holder | 222/396 |
| 3,718,236 | 2/1973 | Reyner et al. | 222/386.5 |
| 3,736,930 | 6/1973 | Georgi | 604/67 |
| 3,756,556 | 9/1973 | Georgi | 251/7 |
| 3,778,971 | 12/1973 | Granger et al. | 96/6 |
| 3,800,794 | 4/1974 | Georgi | 604/52 |
| 3,803,810 | 4/1974 | Rosenberg | 96/6 |
| 3,804,077 | 4/1974 | Williams | 126/263.1 |
| 3,840,009 | 10/1974 | Michaels et al. | 604/892.1 |
| 3,891,509 | 6/1975 | Warren et al. | 435/29 |
| 3,993,061 | 11/1976 | O'Leary | 604/152 |
| 3,994,294 | 11/1976 | Knute | 604/152 |
| 4,012,203 | 3/1977 | Rosiere | 422/236 |
| 4,013,422 | 3/1977 | Spinner | 422/236 X |

(List continued on next page.)

FOREIGN PATENT DOCUMENTS

| | | |
|---|---|---|
| 0509335A1 | 10/1992 | European Pat. Off. . |
| 2687291 | 8/1993 | France . |
| 1270781 | 4/1972 | United Kingdom . |
| WO9207612 | 5/1992 | WIPO . |
| WO9325269 | 12/1993 | WIPO . |

*Primary Examiner*—Kevin P. Shaver
*Attorney, Agent, or Firm*—Knobbe, Martens, Olson & Bear

[57] ABSTRACT

The present invention relates to chemical reactants, compositions, methods to manufacture reactants, and apparatus for the generation of a gas pressure to drive a fluid from an infusion pump at controlled flow rates.

7 Claims, 4 Drawing Sheets

U.S. PATENT DOCUMENTS

| | | | |
|---|---|---|---|
| 4,037,598 | 7/1977 | Georgi | 604/65 |
| 4,043,489 | 8/1977 | Buckman | 222/397 |
| 4,049,158 | 9/1977 | Lo et al. | 222/399 |
| 4,067,332 | 1/1978 | O'Leary | 604/152 |
| 4,080,967 | 3/1978 | O'Leary | 604/152 |
| 4,111,613 | 9/1978 | Sperry | 417/394 |
| 4,137,913 | 2/1979 | Georgi | 604/152 X |
| 4,203,441 | 5/1980 | Theeuwes | 222/386.5 |
| 4,222,127 | 9/1980 | Donachy | 417/394 X |
| 4,235,236 | 11/1980 | Theeuwes | 604/892.1 |
| 4,237,881 | 12/1980 | Beigler et al. | 604/141 |
| 4,331,728 | 5/1982 | Theeuwes | 428/215 |
| 4,335,835 | 6/1982 | Beigler | 222/95 |
| 4,353,887 | 10/1982 | Hess | 424/467 |
| 4,360,131 | 11/1982 | Reyner | 222/399 X |
| 4,373,341 | 2/1983 | Mahaffy et al. | 222/399 X |
| 4,376,500 | 3/1983 | Banks et al. | 222/386.5 |
| 4,379,453 | 4/1983 | Baron | 604/145 |
| 4,382,965 | 5/1983 | Sandine | 426/7 |
| 4,468,220 | 8/1984 | Willbanks | 222/399 X |
| 4,478,044 | 10/1984 | Magid | 222/399 X |
| 4,491,250 | 1/1985 | Liebermann | 222/386.5 |
| 4,507,116 | 3/1985 | Leibinsohn | 604/142 |
| 4,510,734 | 4/1985 | Banks et al. | 53/449 |
| 4,511,355 | 4/1985 | Franetzki | 604/131 |
| 4,513,884 | 4/1985 | Magid | 222/386.5 X |
| 4,518,103 | 5/1985 | Lim et al. | 222/389 X |
| 4,553,685 | 11/1985 | Magid | 222/386.5 X |
| 4,567,948 | 2/1986 | Rozneicki | 169/76 |
| 4,597,959 | 7/1986 | Barr | 424/401 |
| 4,601,893 | 7/1986 | Cardinal | 424/424 |
| 4,618,487 | 10/1986 | DuBois | 424/467 |
| 4,626,241 | 12/1986 | Campbell et al. | 604/49 |
| 4,629,620 | 12/1986 | Lindahl | 424/473 |
| 4,634,430 | 1/1987 | Polaschegg | 604/141 |
| 4,640,445 | 2/1987 | Yamada | 604/145 X |
| 4,646,946 | 3/1987 | Reyner | 222/386.5 |
| 4,648,955 | 3/1987 | Maget | 204/258 |
| 4,663,147 | 5/1987 | DePrince | 424/467 |
| 4,673,392 | 6/1987 | Keime | 604/141 |
| 4,678,661 | 7/1987 | Gergely | 424/44 |
| 4,679,706 | 7/1987 | Magid | 222/386.5 X |
| 4,687,423 | 8/1987 | Maget | 417/379 |
| 4,687,660 | 8/1987 | Baker | 424/465 |
| 4,734,092 | 3/1988 | Millerd | 604/140 X |
| 4,780,117 | 10/1988 | Lahey | 126/263.1 X |
| 4,785,972 | 11/1988 | Lefevre | 222/386.5 |
| 4,802,343 | 2/1989 | Rudick | 62/294 |
| 4,816,262 | 3/1989 | McMullen | 424/467 |
| 4,847,093 | 7/1989 | Ayer | 424/473 |
| 4,869,402 | 9/1989 | Ash, Jr. | 222/386.5 X |
| 4,870,805 | 10/1989 | Morane | 222/394 X |
| 4,886,514 | 12/1989 | Maget | 604/96 X |
| 4,893,730 | 1/1990 | Boldue | 222/402.1 X |
| 4,895,133 | 1/1990 | Collins | 126/263.1 X |
| 4,896,794 | 1/1990 | Banks et al. | 222/386.5 X |
| 4,902,278 | 2/1990 | Maget | 604/132 |
| 4,919,310 | 4/1990 | Young et al. | 222/386.5 |
| 4,923,095 | 5/1990 | Dorfman et al. | 222/386.5 |
| 4,929,214 | 5/1990 | Liebermann | 446/221 |
| 4,969,874 | 11/1990 | Michel | 604/145 X |
| 5,009,340 | 4/1991 | Morane | 222/386.5 X |
| 5,022,564 | 6/1991 | Reyner | 222/399 X |
| 5,032,619 | 7/1991 | Frutin et al. | 222/399 X |
| 5,035,230 | 7/1991 | Steidl | 126/263.1 X |
| 5,035,351 | 7/1991 | Moran | 222/386.5 X |
| 5,053,012 | 10/1991 | Edwards | 604/146 |
| 5,054,651 | 10/1991 | Morane | 222/399 X |
| 5,057,285 | 10/1991 | Belt | 422/236 |
| 5,082,558 | 1/1992 | Burris | 210/167 |
| 5,090,963 | 2/1992 | Gross | 604/132 |
| 5,101,730 | 4/1992 | Bender | 102/288 |
| 5,106,374 | 4/1992 | Apperson et al. | 604/141 X |
| 5,133,701 | 7/1992 | Han | 222/399 X |
| 5,137,186 | 8/1992 | Moran | 222/386.5 X |
| 5,179,982 | 1/1993 | Bérubé et al. | 222/386.5 X |
| 5,301,851 | 4/1994 | Frutin | 222/386.5 X |
| 5,333,763 | 8/1994 | Lane et al. | 222/386.5 |
| 5,342,627 | 8/1994 | Chopra | 424/473 |
| 5,398,850 | 3/1995 | Sancoff | 222/386.5 |
| 5,398,851 | 3/1995 | Sancoff | 222/386.5 |

METHOD FOR GENERATING GAS TO DELIVER LIQUID FROM A CONTAINER

CROSS REFERENCE TO RELATED APPLICATIONS

This application is a divisional of U.S. patent application Ser. No. 08/205,875 filed Mar. 3, 1994, now U.S. Pat. No. 5,398,850, which is a continuation-in-part of U.S. patent application Ser. No. 08/105,327 filed Aug. 6, 1993, now U.S. Pat. No. 5,398,851 and application Ser. No. 08/105,284 filed Aug. 6, 1993, now U.S. Pat. No. 5,397,303, the disclosure of which is hereby incorporated by reference.

BACKGROUND OF THE INVENTION

1. Field of the Invention

The present invention relates to chemical reactants, compositions, methods to manufacture reactants, and apparatus for the generation of a gas pressure to drive a fluid from an infusion pump.

2. Background of the Art

There are several examples in the art of infusion pumps which operate on the use of gas pressure to drive an infusion liquid into a patient. For example, in Baron, U.S. Pat. No. 4,379,453, an infusion bag is equipped with an internal bag including a set of reactive chemicals that when mixed react to form a gas and inflate the internal bag to drive a liquid from the infusion bag. Similarly, in Baron, U.S. Pat. No. 4,379,453 the inventor disposed the reactive chemicals into a cuff-like apparatus to squeeze the liquid from the infusion bag.

The use of gas pressure, without the need for a chemical reaction, has also been demonstrated. See U.S. Pat. No. 5,106,374.

However, in each of the above-described patents, there is a limited ability for an operator to control the pressure of the gas and ultimately the flow rate of the liquid from the device. Baron in U.S. Pat. No. 4,379,453 attempted to solve this problem by utilizing a plurality of reactions. However, this system merely creates two "peaks" in pressure and consequently flow rate.

Accordingly, a need exists in the art for controlled rate infusion devices which can be retrieved through the use of reactive chemicals to generate gas.

SUMMARY OF THE INVENTION

The present invention solves the foregoing problem in the art through the provision of particular chemical reactants, compositions of the chemical reactants, methods to manufacture the chemical reactants, and apparatus that allow for the controlled generation of a gas in, and consequently the flow rate of a liquid from an infusion pump.

In accordance with a first aspect of the present invention there is provided a composition for use in a carbon dioxide generating reaction, comprising an alkalai metal carbonate admixed with a rate limiting amount of a rate controlling moiety and formed into a solid mass. In a preferred embodiment, the alkalai metal carbonate is selected from the group consisting of sodium carbonate, magnesium carbonate, and calcium carbonate. In another preferred embodiment, the rate controlling moiety is selected from the group consisting of polyvinylpyrrolidone, polyethylene glycol, polyvinyl alcohol croscarmellose sodium. Preferably, the mass is partially coated with a material that is nonreactive with a liquid chemical that is reactive with the carbonate to form carbon dioxide. Moreover, preferably, the material is also insoluble in the liquid chemical. In a highly preferred embodiment, the mass is reacted with an effective amount of water to enhance the mechanical properties and hardness of the mass.

In accordance with a second aspect of the present invention, there is provided an apparatus for the generation of a gas to push a liquid from a container, comprising a substantially closed housing having an outside wall in fluid communication with the container, the housing further comprising and separately enclosing an alkalai metal carbonate formed into a solid mass and a liquid chemical that is reactive with the carbonate to form carbon dioxide gas, and means for combining the carbonate and the liquid chemical. Preferably, the alkalai metal carbonate is selected from the group consisting of sodium carbonate, magnesium carbonate, and calcium carbonate. Also, preferably, the liquid chemical is selected from the group consisting of solutions of citric acid and acetic acid. In a preferred embodiment, the mass further comprises a rate limiting amount of a rate controlling moiety admixed with the carbonate. In another preferred embodiment, the mass is partially coated with a material that is nonreactive with a liquid chemical that is reactive with the carbonate to form carbon dioxide. Preferably, the material is also insoluble in the liquid chemical. In a highly preferred embodiment, the mass is reacted with an effective amount of water to enhance the mechanical properties and hardness of the mass. In a preferred embodiment, the combining means comprises a frangible member that is adapted to be pierced upon an application of a force through the outside wall of the housing.

In accordance with a third aspect of the present invention, there is provided an apparatus for the generation of a gas to push a liquid from a container, comprising a hydrophobic membrane surrounding and separately enclosing an alkalai metal carbonate formed into a solid mass and a liquid chemical that is reactive with the carbonate to form carbon dioxide gas, the hydrophobic membrane being positioned in gas communication with the container, and means for combining the carbonate and the liquid chemical. In a preferred embodiment, the alkalai metal carbonate is selected from the group consisting of sodium carbonate, magnesium carbonate, and calcium carbonate. In another preferred embodiment, the liquid chemical is selected from the group consisting of solutions of citric acid and acetic acid. In a preferred embodiment, the mass further comprises a rate limiting amount of a rate controlling moiety admixed with the carbonate. In another preferred embodiment, the mass is partially coated with a material that is nonreactive with a liquid chemical that is reactive with the carbonate to form carbon dioxide. The material is preferably also insoluble in the liquid chemical. In another preferred embodiment, the mass is reacted with an effective amount of water to enhance the mechanical properties and hardness of the mass. In another preferred embodiment, the combining means comprises a frangible member that is adapted to be pierced upon an application of a force through the outside wall of the membrane.

In accordance with another aspect of the present invention, there is provided an improvement in an apparatus for the delivery of an infusion liquid from a container, of the type wherein the apparatus separately includes a first and a second chemical, the first and second chemical being reactive to generate carbon dioxide gas, with the first chemical being disposed in solid form and the second chemical being disposed as a liquid, the improvement comprising the first chemical being admixed with a rate limiting amount of a rate controlling moiety and formed into a solid mass.

In accordance with another aspect of the present invention, there is provided a method to generate carbon dioxide gas for the controlled delivery of a liquid from a container, comprising separately providing a first and a second chemical, at least one of the chemicals enclosed in a first container, the first and second chemicals being reactive to generate carbon dioxide gas upon contact therebetween, providing means for controlling the reaction rate between the first and second chemicals, and means operable to allow the chemicals to come into contact with one another, activating the contact means so that the first and second chemicals come into contact and react to generate the gas, and communicating the gas to means operative to drive the liquid from the second container, wherein, the controlling means acts to continue the reaction for a sufficient length of time to deliver the liquid from the container and the liquid is driven from the container at a substantially constant flow rate.

In accordance with another aspect of the present invention, there is provided a method to generate carbon dioxide gas for the controlled delivery of a liquid from a container, comprising separately providing a first and a second chemical, at least one of the chemicals enclosed in a first container, the first and second chemicals being reactive to generate a gas upon contact therebetween, providing means operable to allow the chemicals to come into contact with one another, and means operable to maintain a predetermined pressure, activating the contact means so that the first and second chemicals come into contact and react to generate a gas such that upon attainment of the predetermined pressure within the first container, the container is maintained at the predetermined pressure through the pressure maintenance means, and communicating the gas to means operative to drive a liquid from a second container at a substantially constant flow rate.

In accordance with another aspect of the present invention, there is provided an improvement in a method to manufacture an apparatus for the delivery of an infusion liquid from a container, the apparatus being of the type wherein a first and a second chemical are separately included, the first and second chemical being reactive to generate carbon dioxide gas, with the first chemical being disposed in solid form and the second chemical being disposed as a liquid, the improvement comprising sterilizing the apparatus with heat.

BRIEF DESCRIPTION OF THE DRAWING FIGURES

FIG. 1. is a top perspective view of a preferred solid reactant tablet in accordance with the invention.

FIG. 2. is a top perspective view of a preferred solid reactant tablet coated with an insoluble sealant in accordance with the invention.

FIG. 3. is a cross-sectional view of the tablet in FIG. 2 along line 3—3 that is partially reacted.

FIG. 4. is a top perspective view of a preferred solid reactant tablet coated with an insoluble sealant in accordance with the invention.

FIG. 5. is a cross-sectional view of the tablet in FIG. 4 along line 5—5 that is partially reacted.

FIG. 6. is a top perspective view of a preferred solid reactant tablet coated with an reaction slowing coating with a portion of the tablet cut away to show the variable thickness of the coating on the tablet in accordance with the invention.

FIG. 7. is a cross-sectional side view of a preferred device that operates and provides a reaction rate controlling environment in accordance with the present invention.

FIG. 8. is a cross-sectional side view of the device in FIG. 7 showing the mode of operation.

FIGS. 9a and 9b are schematic cross-sectional views of a pressure relief valve in accordance with the invention.

FIG. 10. is a graph showing the substantially linear flow rate profile generated in accordance with the present invention in comparison to reactions operated with the control features of the present invention.

DETAILED DESCRIPTION OF THE PREFERRED EMBODIMENTS

Figure 1:
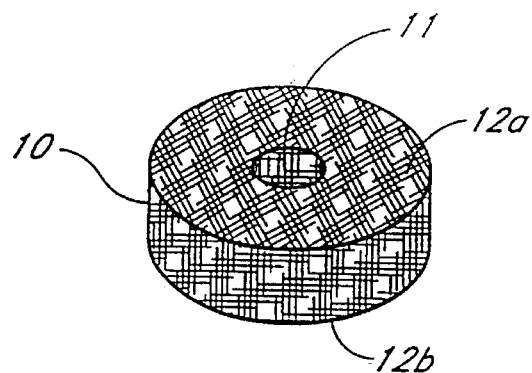

In accordance with the invention, there are provided chemical reactants, compositions of the chemical reactants, methods to manufacture chemical reactant compositions, and apparatus to ensure the controlled generation of a gas from a gas generating reaction in order to provide a substantially constant flow rate of a liquid from an infusion pump. In general, infusion pumps in which the present invention is particularly useful are disclosed in copending U.S. patent application, Ser. Nos. 08/105,327 and 08/105,284, the disclosures of which are hereby incorporated by reference. The infusion pumps disclosed therein generally include a housing divided into a liquid reservoir and a gas expansion reservoir with a membrane disposed therebetween. The membrane ordinarily extends substantially into the gas expansion reservoir when the pump is filled with a liquid in the liquid reservoir. Thus, when gas expands within the gas expansion reservoir, the membrane is pushed into the liquid reservoir, displacing liquid. In a preferred embodiment, the gas expansion reservoir is in communication with a gas generation reactor. The gas generation reactor separately houses the reactive chemicals.

As will be appreciated, the control aspects of the present invention are equally applicable with respect to other infusion pump designs and would be expected to operate more effectively than previous designs.

Chemical Reactants

In accordance with the present invention, there are provided chemical reactants that are used effectively to generate a gas to push a fluid from an infusion pump. In order to generate carbon dioxide, two or more reactive chemicals are mixed that upon reaction generate a gas. Preferably, one of the reactants is provided in liquid form, i.e., a liquid chemical, a solution, or the like, and another one of the reactants is provided as a solid. Either the liquid or the solid may comprise more than one reactive chemical. However, for simplicity, often, each of the liquid and the solid contain only one reactive species.

Preferably, the gas generated is carbon dioxide. Carbon dioxide is generally quite inert and safe at low concentrations. However, other gases could also be used, provided they are relatively inert and safe.

For the purposes of the following discussion, it will be assumed that carbon dioxide is to be generated. As mentioned above, to generate the gas, at least two reactants are caused to come into contact. For ease of reference, the reactants will be referred to herein as a first reactant and a second reactant or a solid reactant and a liquid reactant and, particular sets of reactants will be referred to as reactant sets.

First Reactant

Preferably, the first reactant is selected from the group consisting of carbonates and bicarbonates, particularly, Group I and II metal carbonates and bicarbonates (the "carbonate"). For example, preferred carbonates include sodium bicarbonate, sodium carbonate, magnesium carbonate, and calcium carbonate. However, sodium bicarbonate, sodium carbonate and calcium carbonate are highly preferred, with sodium carbonate (or soda ash) being the most highly preferred. A desirable feature of sodium carbonate is that it is easily sterilizable. For example, sodium carbonate can be sterilized with heat, such as through autoclaving. This is preferable, since the infusion devices for use with the invention are designed for animal use and it is safer to ensure that all of the components are sterile whether it is expected that they will come into contact with the patient or not. Other reactants that are sterilizable with heat are equally useful.

The carbonate can be either used as a solid reactant or can be dissolved in a solution to form a liquid reactant. In a preferred embodiment, the carbonate is used as a solid. The reason for this choice is that the carbonates are all solids and some are only sparingly soluble in water.

Second Reactant

The second reactant is preferably an acid. Preferably, the acid is selected from the group consisting of acids, acid anhydrides, and acid salts. Preferably, the second reactive chemical is citric acid, acetic acid, acetic anhydride, or sodium bisulfate.

Usually the second reactant is used as the liquid reactant. However, in the case of citric acid and sodium bisulfate, for example, the second reactant can also be the solid reactant. Nevertheless, generally the second reactant is more soluble in water than the first reactant and is, therefore, used to form the liquid reactant.

Reactant Sets

A reactant set is based upon a variety of considerations. For example, the solubility of the first and second reactants are considered to determine which reactant should be used as the solid or liquid reactant. Also considered is the product of the reaction and its solubility. It is preferred that the products be $CO_2$ gas and a soluble inert compound. Once these factors are considered, appropriate reactant sets can be constructed. For instance, as will be appreciated, in preferred embodiments, reaction sets such as those shown in Table I are preferred:

TABLE I

| Solid Reactant | Liquid Reactant |
| --- | --- |
| Sodium Carbonate | Citric Acid |
| Calcium Carbonate | Acetic Acid |
| Magnesium Carbonate | Citric Acid |

Once the appropriate reactant sets are established, it is important to determine the operating parameters that will be necessary to control the generation of the gas and, therefore, provide a substantially constant flow rate. As will be appreciated, the mere reaction of the solid reactant as a powder and the liquid reactant in the above reactant sets in the atmosphere at standard temperature and pressure, will liberate gas at the maximum kinetic rate for the reaction.

When enclosed under some pressure and under a $CO_2$ atmosphere, the kinetics will be slowed. Nevertheless, a flow rate of a liquid driven from a pump by the gas, upon reaction of the first and second reactants without any other control, will not be substantially constant. Rather, the flow will initiate, increase rapidly, level off, and then subside.

Accordingly, we unexpectedly discovered that through the introduction of certain control parameters, the rate of generation of a gas can be controlled and the flow rate from an infusion pump can be maintained at a substantially constant rate. The control parameters include the structure or geometry of the solid reactant, the composition of the solid reactant, and solid reactant surface modifications. An additional control parameter is in the environment of the reaction.

Solid Reactant Structure and Geometry

The reason that the solid reactant structure and geometry will affect the reaction rate of the solid and liquid reactant is because the structure or geometry affect access between the reactants. For example, in a preferred embodiment, the solid reactant is formed into a geometric mass from the powdered chemical. Rather than having tiny granules or powdered reactant reacting simultaneously with the liquid reactant, the solid mass will react only at the surface and additional solid reactant will become available as only product and gas are formed and the product is dissolved as the reaction progresses.

Thus, in a preferred embodiment, the solid reactant is formed into a solid mass. Any geometric shape can be used, although, it is preferred to choose a shape that will possess a surface area that provides a substantially constant reaction rate. Thus, spherical, pyramidal, tetrahedral, cylindrical, rectangular, and like shapes could all be utilized. Each geometry will provide slightly different gas generation patterns. In a highly preferred embodiment of the invention, the solid reactant 10 has a cylindrical shape. See FIG. 1. This shape is chosen for illustrative purposes because of its simplicity to prepare. For example, a commercially available drug tablet press can be utilized. The tablet 13 is preferably compressed to between 7000 and 8000 psi.

The illustrated embodiment of the solid reactant in FIG. 1 includes an additional feature that operates to assist in keeping a substantially constant surface area of the solid reactant in reactive contact with the liquid reactant. This feature is the bore 11 that extends between the two circular surfaces 12a and 12b in the solid reactant 10. Gas bubbles, in appropriate circumstances, can cling to the solid reactant 10 and prevent further reaction between the liquid reactant and the solid reactant 10. The bore 11 allows generated gas to vent from the lower circular surface 12b through the solid reactant 10. This assists in keeping the solid reactant 10 in contact with the liquid reactant.

It will be appreciated, therefore, that a variety of gas generation profiles are available through varying the geometry or structure of the solid reactant. The basic profile will be determined, essentially, by the total surface area in reactive contact with the liquid reactant and how steadily the surface area changes as the reaction progresses. The greater the surface area of the solid reactant in reactive contact with the liquid reactant will generally cause a faster generation of gas. The smaller the surface area in reactive contact with the liquid reactant will generally cause a slower generation of gas. Thereafter, the change in the surface area of the solid reactant in reactive contact with the liquid reactant will determine the continued gas generation profile. Of course, both the size of the solid reactant and its relative and absolute surface area will affect the gas generation profile.

The gas generation profile roughly translates into the flow rate profile as a liquid is driven from a pump. As was mentioned previously, there is a small correction required for the amount of gas and its pressure in varying the kinetics of the reaction between the solid reactant and the liquid reactant.

Solid Reactant Mechanical Properties

As will be appreciated, there are a variety of ways to enhance the mechanical, physical, and chemical properties of a solid reactant. One method is to treat or form the solid reactant with chemical moieties that lend desired properties. In a critical area, it is desirable for the solid reactant to retain sufficient mechanical strength so as not to fall apart and lose the ability to enter into controlled gas generation.

In a preferred embodiment, the solid reactant is surface treated with a material that enhances its mechanical strength. In a highly preferred embodiment, for example, where the solid reactant is sodium carbonate, this can be accomplished through the application of water to the solid reactant after it has been formed into the appropriate geometric shape and size. The water forms sodium carbonate hydrates on at least a portion of the sodium carbonate solid reactant and creates a tablet with mechanical strength similar to plaster, yet does not limit the ability of the solid reactant to participate in the gas generation reaction with the liquid reactant. In contrast, a tablet made from sodium carbonate without the application of water results in a solid reactant that has a propensity to crumble over time and lose its controllability.

Compositions

In addition to the structure or geometry of the solid reactant, the composition of the solid reactant can be modified to slow the dissolution of the solid reactant or slow the rate at which it becomes accessible to the liquid reactant, which, in turn, slows the rate at which the solid reactant becomes available for reaction. Thus, the composition of the solid reactant can be used to vary the gas generation profile of, and, consequently, the flow rate profile from, the reaction between the solid reactant and the liquid reactant.

In a preferred embodiment, the composition of the solid reactant is modified through the addition of a material that acts to slow the rate at which solid reactant becomes available for reaction with the liquid reactant. In another embodiment, the solid reactant is modified through the addition of a material that acts to slow the dissolution of the solid reactant. Essentially, such materials each act to "dilute" the amount of the solid reactant at any one time in reactive contact with the liquid reactant.

Moieties that can be admixed in the solid reactant and act to control the reaction rate between the liquid reactant and the solid reactant are referred to herein as rate controlling moieties. Rate controlling moieties include fillers and binders. Fillers or binders are quite effective to slow the reaction rate or limit the access of the liquid reactant to the solid reactant. Examples of suitable fillers or binders include polyvinylpyrrolidone (i.e., PLASDONE, available from ISP Technologies, Inc., Wayne, N.J.), polyethylene glycol (i.e., PEG 400 available from Olin Corp., Stamford, Conn.), and polyvinyl alcohol (i.e., PVA 205S available from Air Products, Allentown, Pa.), Ac-Di-Sol® Goscarmellose Sodium (cross-linked sodium carboxymethylcellulose) (available from FMC Corporation, Philadelphia, Pa.). Similarly, there are a large number of excipients or carriers that will act to slow the chemical reaction.

Alternatively, as will be appreciated, it is possible to vary the concentration of the liquid reactant in order to modify the reaction rate with the solid reactant.

The rate controlling moiety is included in an amount effective to control the reaction rate between the solid and liquid reactant. Typically, amounts that are effective to control the reaction rate are in the range of from about 0.5% to about 50% by weight of the solid reactant, more preferably from about 1% to about 20% or about 2% to about 15% or about 2.5% to about 7% by weight. In highly preferred embodiments, the rate controlling moiety is included in the range of from about 3% to about 6% by weight.

Solid Reactant Surface Modifications

It is also possible to modify the surface of the solid reactant in order to limit the access of the liquid reactant to the solid reactant. For example, the solid reactant can be partially coated with a material that is insoluble in the liquid reactant and that protects the surface that is coated from reactive contact with the liquid reactant. Exemplary materials that are useful as insoluble surface treatments include a room temperature vulcanizing (RTV) silicone adhesive, such as PERMATEX®, available from Loctite Corporation, Cleveland, Ohio (Part No. 66B), and a polyurethane coating (available from B.F. Goodrich).

Figure 2:
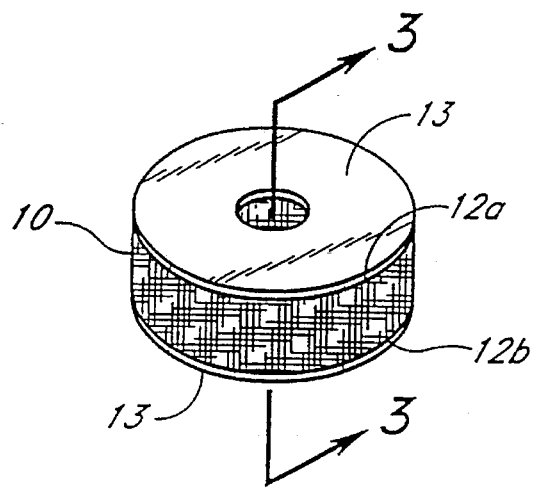
Figure 3:
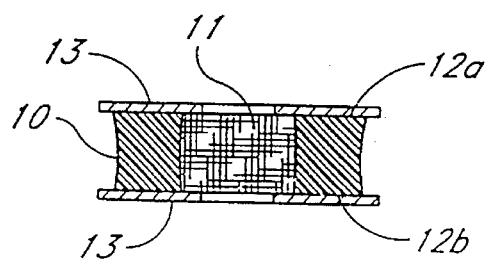

An example of this strategy is shown in FIG. 2. There, the solid reactant 10 is coated on its top and bottom surfaces 12a and 12b with a sealant 13. The sealant 13 prevents the top and bottom surfaces 12a and 12b of the solid reactant 10 from being dissolved and reacting with the liquid reactant. In FIG. 3, a partially reacted solid reactant having the sealant 13 coating the top and bottom surfaces 12a and 12b is shown in cross-section. The view in FIG. 3 is taken along line 3—3 in FIG. 2. As will be seen, the bore 11 has grown in diameter, whereas the diameter of the solid reactant 10 is reduced. The sealant is still positioned on the remaining solid reactant 10.

Figure 4:
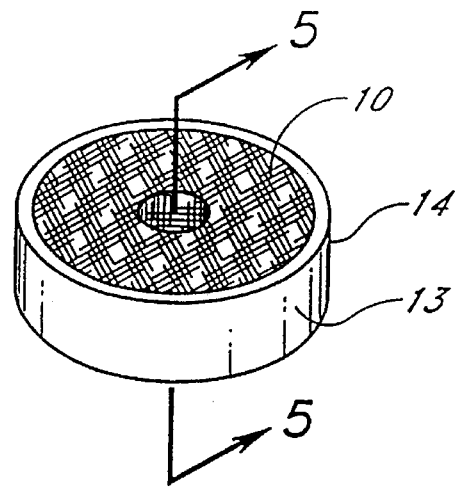
Figure 5:
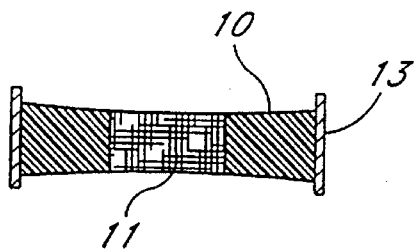

Alternatively, in FIG. 4, the solid reactant 10 is shown with an sealant applied around the periphery 14. This configuration requires that the top and bottom surfaces be preferentially dissolved. In FIG. 5, a partially reacted solid reactant having the sealant 13 coating the periphery 14 is shown in cross-section. The view in FIG. 5 is taken along line 5—5 in FIG. 4. As will be seen, the bore 11 has grown in diameter, whereas the thickness of the solid reactant 10 is reduced.

In each case, it will be appreciated that the sealant or other surface modification that causes preferential reaction between a portion of the solid reactant and the liquid reactant allows greater control over the generation of gas from the reaction. The process acts to predictably expose a given surface area of the solid reactant to the liquid reactant. Accordingly, control is achieved over the gas generation profile and correspondingly the flow rate profile of a pump including such reactants with surface modifications.

An additional surface modification that can be used as an alternative or additional control on the access of the liquid reactant to the solid reactant is the utilization of a delayed reaction coating. In general, a delayed reaction coating in accordance with the invention is a coating that serves to temporarily limit or eliminate the exposure of the solid reactant to the liquid reactant. An object of such limitation is to minimize any initial effervescence from the reaction of the solid reactant with the liquid reactant.

Figure 6:
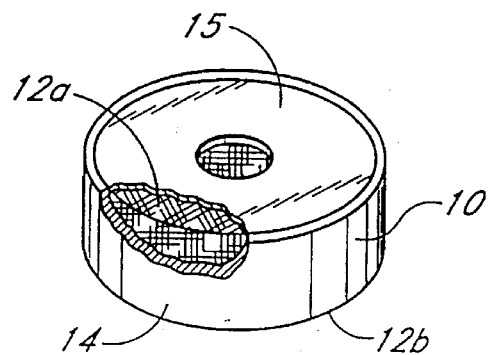

One material that can be used with success to achieve such limitation is a binder or filler, as described above, applied to the outside of the solid reactant as is shown in FIG. 6. In FIG. 6, the solid reactant 10 has a layer of coating 15, such as PLASDONE, applied uniformly over the top and bottom surfaces 12a and 12b. A thicker layer of the coating 15 is applied to the periphery 14. Upon mixing the coated solid reactant with the liquid reactant, the coating 15 on the top and bottom surfaces 12a and 12b will dissolve more quickly than the coating on the periphery 14. Thus, the gas generation reaction will be initiated on the top and bottom surfaces 12a and 12b before the reaction on the periphery 14 is initiated. In general, the gas generation profile in this reaction will show a two step increase in the gas generated as first one surface area of the solid reactant 10 is in reactive contact with the liquid chemical, followed by an increased surface area in reactive contact when the coating 15 is dissolved from the periphery 14. Consequently, the flow rate profile achieved will begin at a first rate and accelerate to a second rate.

This latter control mechanism can be used in conjunction with the non-reactive tablet coating, i.e., the sealant described above to achieve selected gas generation and flow rate profiles.

As will be appreciated, the sealant can be applied in a variety of patterns, shapes, or contours, any one of which is contemplated in accordance with the invention. However, for simplicity and for ease in determining the actual and effective surface area of the solid reactant that is exposed as well as for purposes of repeatability, it is often desirable to choose a relatively simple and consistent pattern and to stay with it.

Reaction Environment

In addition to the above-described modifications that can be accomplished with respect to the solid and liquid reactants, it is also possible to enhance the controllability of gas generation reactions through appropriate selection of the environment in which the reactions occur. The environmental features that assist in control over gas generation control are (i) the conduct of the gas generation reaction within a confined space, wherein the solid reactant and the liquid reactant are able to stay in reactive contact regardless of movements of the pump and the like and (ii) control over the operating pressure that is exerted on the liquid to be dispensed so as to provide complete control over the flow rate, regardless of minor fluctuations in the quantity of, or rate at which the, gas is generated.

Figure 7:
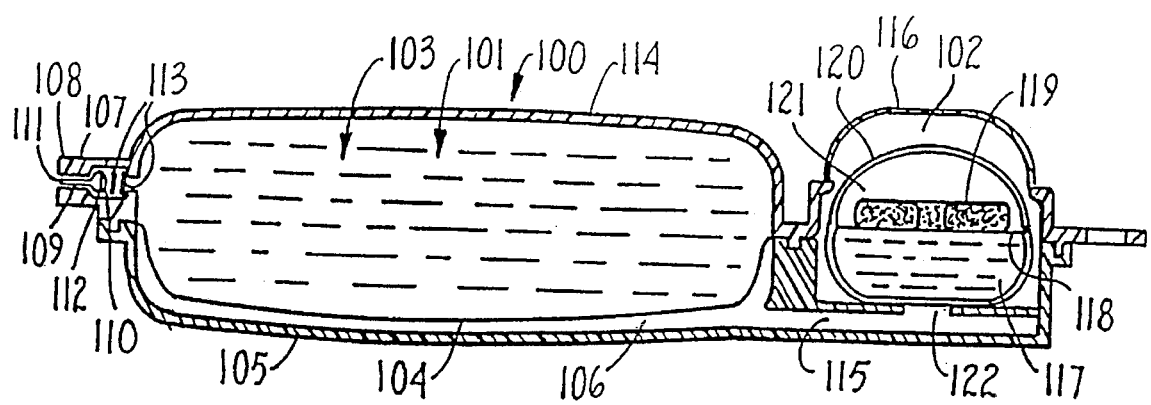
Figure 8:
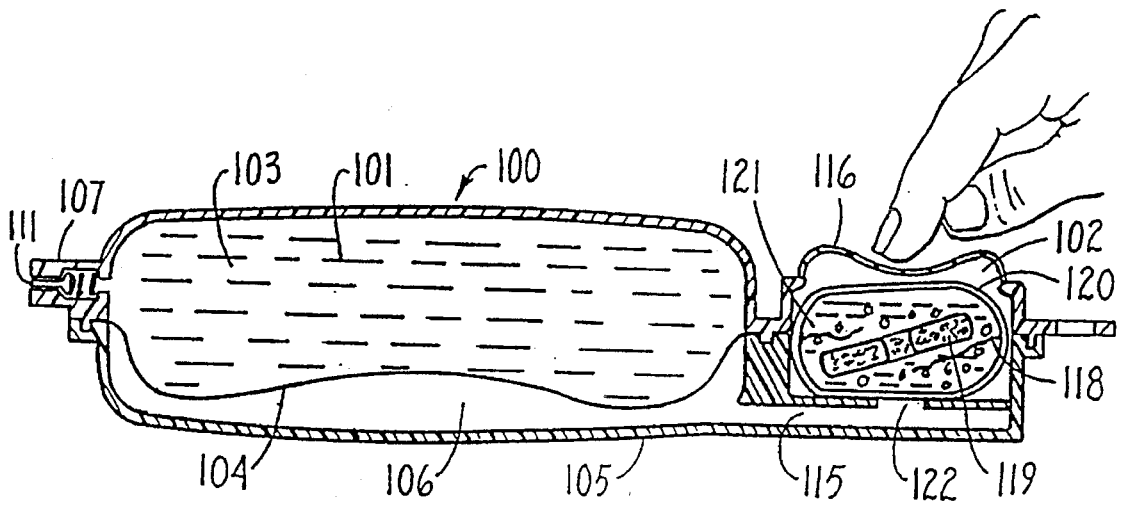

In accordance with the present invention, preferably, the gas generation reaction is conducted within a confined space. One way that this is accomplished is through the use of a separate gas generation housing. A device showing a separate gas generating housing is shown in FIGS. 7 and 8, which is a cross-sectional side view of an infusion device of the present invention. The device 100 is of a rectangular shape with rounded edges. It is separated into two separate compartments: the fluid delivery compartment 101 and the gas generation compartment 102. The fluid delivery compartment contains the liquid 103, that may contain a medication, that is to be delivered to a patient. Also within the fluid delivery compartment is the flexible membrane 104. The flexible membrane 104 is held in proximity to (or distended towards) the outer wall 105 in the lower section of the device 100 by the liquid 103. The flexible membrane 104 may contact the outer wall 105, or it may have a slight space 106 (as pictured).

Preferably, the liquid 103 is additionally kept within the fluid delivery compartment 101, by a one-way valve 107, that generally has an outer body 108 with an encircled plunger 109. The plunger 109 typically has a proximal end 110 and a distal end 111 (in relation to the fluid delivery compartment 101). The proximal end 110 of the plunger 109 is typically larger than the distal end 111. Further, the outer body 108 of the valve 107 has a concentric ridge 112 so that the larger proximal end 110 of the plunger 109 abuts the ridge 112, preventing the liquid 103 from flowing through the valve 107. Additionally, the valve 107 can have biasing means, such a spring 113, that forces the proximal end 110 of the plunger 109 distally toward the ridge 112, thereby further aiding in preventing the liquid 103 from flowing through the valve 107.

The valve 107 can be specially manufactured or can be a standard one-way luer fitting, such as those that are commercially available. For example, the Halkey-Roberts Corporation (St. Petersburg, Fla.) produces a variety of luer syringe check valves that can be used for this purpose. We prefer to use Halkey-Roberts Model No. V24200.

It is preferred that all materials that are in contact with the liquid 103 in the fluid delivery compartment 101, such as the flexible membrane 104, the wall 114, and the valve 107 (and it components) be constructed of materials that are non-leaching and are appropriate for medical use. One example of such a material is ultrapure polypropylene and other similar materials. In U.S. Pat. No. 4,803,102 one formulation of ultrapure polypropylene is described. Thinner preparations of ultrapure polypropylene (i.e., 0.002 to 0.010 inch gauge) are used in preparing the flexible membrane 104 and thicker gauge materials (i.e., molded to 0.030 to 0.060 inch gauge) are preferred for making the casing (defined by walls 105 and 114). Further, the flexible membrane 104 is preferably constructed to be gas impermeable, i.e., impermeable to the gas that is generated in the reaction between the solid reactant and the liquid reactant described above. In order to attain gas impermeability in the membrane, either a gas impermeable material, such as polyvinylindene dichloride or polyether terephthalate can be used or a composite membrane or bi- or multi-layer membrane can be prepared. For example, the surface of the membrane in contact with the liquid 103 in the fluid delivery compartment 101 can be prepared from ultrapure polypropylene, as described above, while the surface in communication with the gas generation compartment 102 can be prepared from polyvinylindene dichloride or polyether terephthalate.

The gas generating compartment 102 is in fluid communication with the fluid delivery compartment 101 through a channel 115 and hole 122. Thus, when gas is generated in the gas generating compartment 102 it will travel through the channel 115 either filling or making the space 106 in the fluid delivery compartment 101. The gas generating compartment 102 additionally comprises a depressible membrane 116 which is sealingly joined to the case of the device 100. The depressible membrane sits above the gas generating compartment 102. Inside the gas generating compartment 102 are the reactants for generating the gas. Shown in this embodiment is a liquid reactant 117 that in a preferred embodiment is contained within a breakable sack 118. Above the sack rests, in this embodiment, a solid reactant pellet 119.

In a highly preferred embodiment, the liquid reactant 117 is a solution of citric acid (0.5 gm/ml (2.6M)), i.e., 12 ml, and the solid reactant is a sodium carbonate "donut shaped" pellet, formed using a tablet or pill press, of the shape shown in FIG. 1. In the pellet, preferably 4.39 grams of sodium carbonate is mixed with 5% by weight of a filler, polyvinylpyrrolidone (PLASDONE, available from ISP Technologies, Inc., Wayne, N.J.) to make a 4.62 gm pellet. Moreover, preferably a polyurethane sealant was applied around the periphery, as shown in FIG. 4, so as to reduce the surface area of the sodium carbonate and filler that would be exposed to the citric acid solution.

Also, in this embodiment, the reactants are contained within a pouch 120. The pouch 120 in a highly preferred embodiment is composed of a hydrophobic material. Hydrophobic materials generally will contain liquids but will allow gases to pass, provided, some of their surface is not covered by the liquid. Hydrophobic materials are typically formed from polymeric materials. Generally, they are formed into a membrane. Examples of useful hydrophobic materials for preparing the pouch 120 are such materials as Tyvek® 1073B (Dupont), Versapel® 450 (Gelman), Goretex® 0.45µ polypropylene bucking, Celguard 2400 (Hoechst-Celanese), Porex® (a hydrophobic scintered polypropylene), and 3M BMF™ (Minnesota Mining and Manufacturing).

As will be understood, the use of a hydrophobic pouch 120 is very useful in that it contains the reactants within the gas generating chamber 102. This fact reduces concerns that the reactants could mix with the liquid in the fluid delivery compartment 101. However, it is critical to note that, as mentioned, the hydrophobic pouch 120 will release gas only so long as a gas pocket 121 exists. Therefore, the hydrophobic pouch must be carefully designed to ensure that the gas pocket 121 is maintained throughout the course of the reaction. If the gas pocket 121 were not present, the pouch 120 would burst and the contents (particularly the liquid reactant 117) of the gas generating compartment 102 would spill into the fluid delivery compartment 101 through the channel 115 and the hole 122. Since the liquid reactant 117 would no longer be in substantial contact with the solid reactant 119, the reaction would essentially terminate and limited additional gas would be evolved. However, as will be appreciated, because of the generation of gas through the reaction, there will be a tendency for the pouch 120 to reinflate and sparge gas, prior to failure.

An additional advantage to the use of the hydrophobic pouch is the fact that it enables the device 100 to be used in any orientation. The reactants in the gas generating chamber 102 are physically separated from the fluid delivery compartment 101 and the liquid 103, and no matter what orientation the device is moved to (so long as the gas pocket 121 exists) gas will continue to be delivered to the fluid delivery compartment 101. This makes the device 100 very versatile. For example, medical personnel do not have to carefully orient the device 100 and ambulatory patients can carry the device in their pockets.

It will be appreciated that the advantage associated with the hydrophobic pouch (i.e., allowing the orientation of the pump to be an insubstantial consideration since the chemical reactants will not get near the fluid to be delivered to the patient and allowing the chemical reactants to stay in contact with one another so as to continue the chemical reaction therebetween) can be achieved through a number of other mechanisms. In general, therefore, any mechanism that allows the gas generated by the reaction between the reactants to be communicated to the pump while the chemical reactants remain in contact away from the pump can be used. Non-limiting examples of such mechanisms include, in addition to the hydrophobic pouch mentioned above, placing the reactants in a float or on rollers in a container so that the reactants remain in the container despite the orientation; use of a hydrophobic membrane in a lumen in communication with a reactant chamber and a pump chamber; lining a container, otherwise sealed, with a hydrophobic material extending above any liquid level and providing a lumen from the container, behind the hydrophobic material, to communicate with the pump.

However, returning the embodiment shown in FIG. 8, in order to operate the pump in this embodiment, a user can simply depress the depressible membrane 116 down into the gas generating compartment 102 with their index finger, for example. This action will force the hydrophobic pouch 120 down onto the solid reactant 119. Such action will break the sack 118 that contained the liquid reactant 117. The chemicals will react and gas will be generated. Provided, as mentioned above, that the gas pocket 121 is maintained, gas will flow through the hydrophobic pouch 120 and be communicated through the hole 122 into the channel 115 and into the fluid delivery compartment 101. Thereafter, provided that the valve 107 is opened through manually depressing the distal end 111, proximally, liquid 103 will begin to flow through the valve 107. As gas continues to be generated the flexible membrane 104 will be displaced away from wall 105 increasing the size of the space 106 between the wall 105 and the flexible membrane 104 as the liquid 103 is delivered out of the device 100.

In a preferred embodiment, the hole 122 or the channel 115 comprise a calibrated orifice. The calibrated orifice is used as the determining factor in flow rate determination, essentially establishing a back-pressure against which the device must work to deliver fluid. It will be appreciated that smaller orifices will result in higher back pressures and slower flows and larger orifices will result in reduced back pressures and higher flows.

Figure 9A:
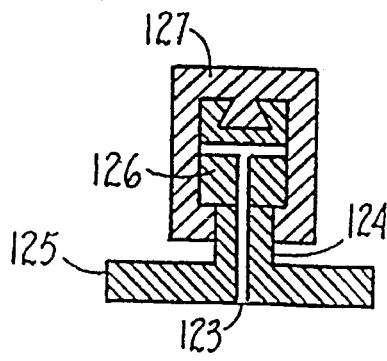
Figure 9B:
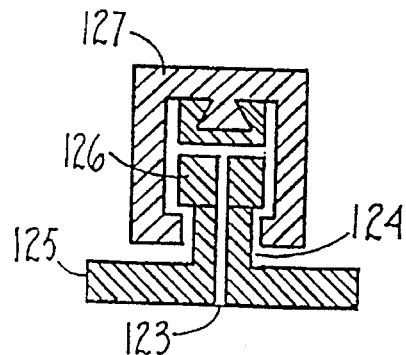

As an additional control feature and for safety, a preferred embodiment of the present invention further includes a pressure relief valve. A simple, but highly effective, pressure relief valve is shown in FIGS. 9a and 9b. The pressure relief valve is in communication with the gas generating chamber through a gas channel 123. The gas channel extends through the casing 125 of the device into a stem 124 that is topped by a mandrel 126. The mandrel 126 is topped by an elastomeric material 127 that concentrically and sealingly surrounds the mandrel 126 as shown in FIG. 9a. The elastomeric material is essentially similar to a silicone rubber septum that folds over, surrounds, and seals around the mandrel 126. While the system operates at preferably 10 psi or less, the elastomeric material 127 will not allow gas to escape. However, when the system exceeds 10 psi, the gas will force out the sides of the elastomeric material 127 allowing gas to escape as shown in FIG. 9b.

Figure 10:
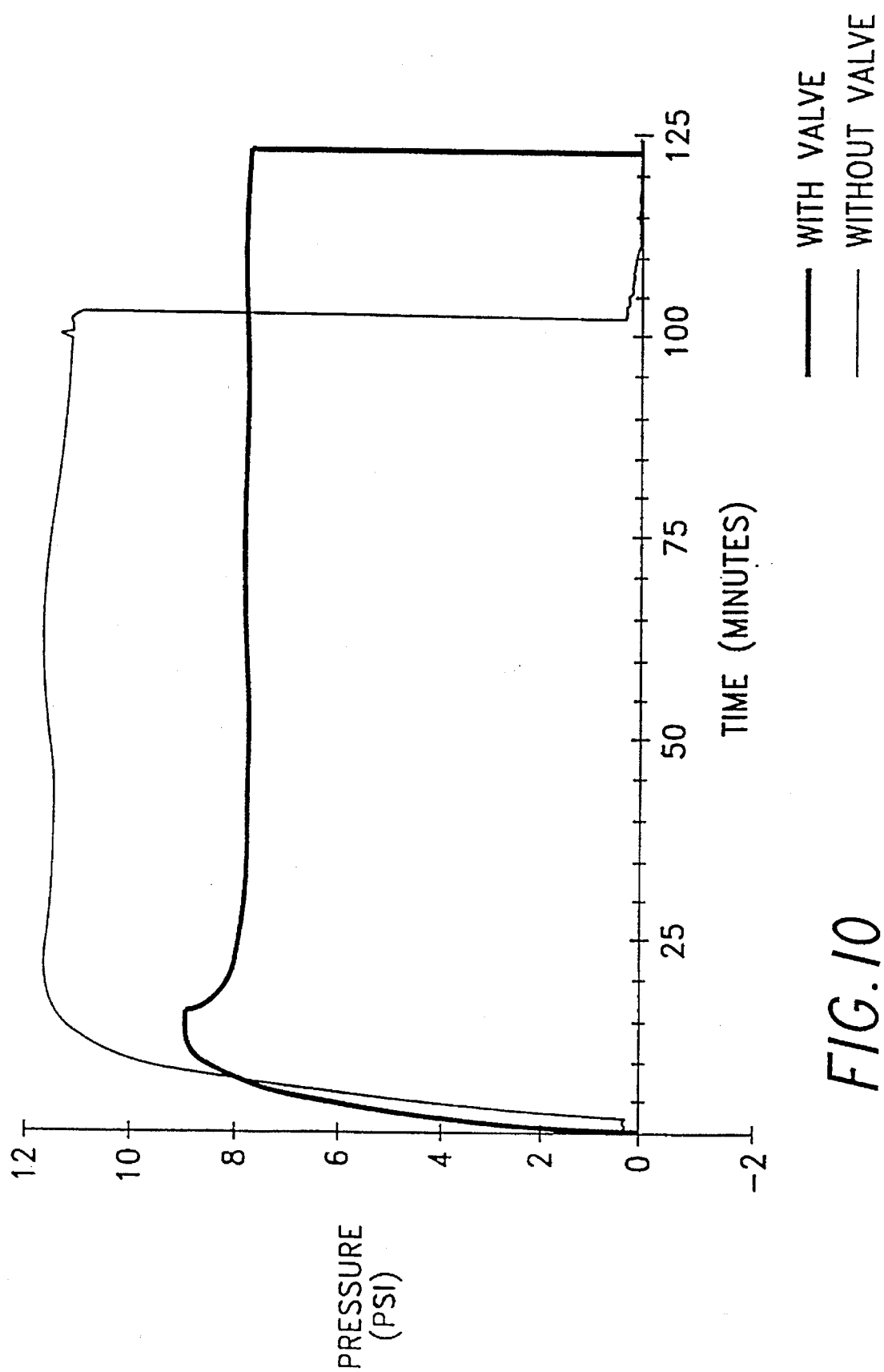

We have discovered that use of the pressure relief valve in combination with the citric acid/sodium carbonate, Plasdone, and coated pellets, as described above, we can achieve an almost completely linear pressure profile as is shown in FIG. 10. Such a linear pressure profile gives rise to an almost perfectly linear flow rate of fluid from the pump.

It will now also be appreciated that a variety of additional features could be added to the pressure relief valve of the present invention in order to lend greater control and conserve gas pressure. For example, the pressure relief valve shown in FIG. 9 could be replaced by a balloon or other pressure/gas reserve mechanism. There are, for instance, inelastic balloon structures that do not show enhanced pressure at reduced diameters. Such materials could be attached to the mandrel 126 in FIG. 9 to capture excess gas. As well, simple two way regulators can be readily conceived of by those of ordinary skill in the art to remove excess gas at a given pressure from the system and introduce gas back to the system when the pressure falls below a certain, predetermined pressure.

As will now be seen, the conduct of the reaction within a confined space and the use of a pressure relief valve are significant in adding yet another degree of control to the generation of gas in accordance with the invention. Where a pressure relief valve is utilized, it is important that sufficient quantities of reactants be used in order that the sparging of any excess gas does not end the reaction before all of the liquid is dispensed from the pump. Accordingly, in a preferred embodiment, sufficient quantities of reactants are included to sustain the generation of gas for a period of time that is effective to dispense substantially all of the fluid from the pump.

As will now be appreciated, through the use of a pressure relief valve, in theory, an otherwise uncontrolled reaction can be used to attain a substantially constant flow rate from the pump.

As will also now be appreciated, confining of the reactants does not necessarily have to be accomplished in a different physical space. For example, the reactants may be separately disposed into a hydrophobic pouch, as described above, and placed anywhere where the gas emerging therefrom would expand a membrane and cause a liquid to be dispensed from a pump. This brings to thought that prior art devices can be easily modified in accordance with the structural teachings of the present invention to enable the attainment of substantially constant flow rates, which was previously not possible.

Quantity of Reactants for Attainment of Specific Flow Rates

In order to tailor devices prepared in accordance with the present invention to particular applications, it is preferable that a user or designer establish a minimum and maximum of reactants that will be necessary to attain a given flow rate over a given period of time. It will be appreciated that in certain infusion applications it is preferable to have relatively low flow rates, whereas in other applications relatively higher flow rates are preferable. Pumps prepared in accordance with the present invention can be prepared to generate flow rates from as low or lower than 2 ml. per hour to upwards of 200 ml. per hour. Particularly preferred flow rates are in the range of from about 5, 10, 15, 20, 50, 100, 150, or 200 ml. per hour. Therefore, a pump can be prepared with sufficient chemical reactants to allow only a fluid flow rate of 5 or 10 ml. per hour. Or, the pumps can be similarly prepared to provide a flow rate of 150 or 200 ml. per hour.

To attain any particular rates, a flow rate profile should be settled upon. The flow rate profile will govern the tablet or solid reactant design, including, the use of fillers, non-reactive skin modifications, delayed reaction coatings, and tablet size and geometry. In connection with consideration of the flow rate profile, the desired start-up speed (i.e., the rate at which the gas generation reaction attains static operating pressure), the length of the delivery that is required and the quantity that is required to be delivered during the time period (i.e., 10 ml./hr. for 20 hours versus 20 ml./hr. for 10 hours; in each instance requiring delivery of 200 ml but in different time periods), and any additional factors, such as flow rate steps and the like, should be considered.

As an additional consideration, as mentioned above, in order to attain particular flow rates, a calibrated orifice is utilized to attain a particular flow rate under particular reaction conditions.

Once the above-essential elements are determined, a user can extrapolate the required amounts of reactants from the following table:

TABLE II

| Sodium Carbonate (shape: FIG. 1) | Citric Acid | Filler | Sealant | Reaction Length | Maximum Accurate Flow Rate |
| --- | --- | --- | --- | --- | --- |
| 5.25 gm | 5.00 gm | 0.25 gm | Yes | 120 min | 200 ml/hr |
| 5.25 gm | 5.00 gm | 0.20 gm | Yes | 70 min | 200 ml/hr |
| 5.25 gm | 4.00 gm | 0.23 gm | Yes | 70 min | 100 ml/hr |
| 4.50 gm | 5.00 gm | 0.25 gm | Yes | 100 min | 200 ml/hr |
| 4.50 gm | 4.50 gm | 0.23 gm | Yes | 90 min | 200 ml/hr |
| 4.00 gm | 4.00 gm | 0.25 gm | Yes | 65 min | 100 ml/hr |
| 4.00 gm | 4.00 gm | 0.20 gm | Yes | 60 min | 100 ml/hr |

Alternatively, a user can perform certain empirical tests to determine the necessary operating conditions for a particular application. Such experiments can be run as described below:

Reaction Length

Side-by-side tests can be run with tablets constructed in accordance with FIG. 2 having varying quantities of solid and liquid reactants and binders in containers (i.e., erlenmeyer flasks) which are closed after the reaction is initiated with a one-hole stopper having a tube running into individual upside down beakers filled with, and in a pool of, water. The gas generated in the reaction will displace the water from the beaker and the time for the complete reaction can be measured to give the reaction length.

Flow Rate

Once the reaction length is known for a chosen composition, a general flow rate can be readily determined through measuring the length of time required to displace a given quantity of liquid. For example, a graduated cylinder can be filled with, and placed upside down in a pool of, water and displacement can be measured as described for reaction length.

What we claim is:

1. In an apparatus for the delivery of a liquid from a container, of the type wherein the apparatus includes a first and a second chemical, the first and second chemical being reactive to generate carbon dioxide gas, with the first chemical being disposed in solid form and the second chemical being disposed as a liquid, the improvement comprising:

the first chemical being admixed with a rate limiting amount of a rate controlling moiety and formed into a solid mass.

2. A method to generate carbon dioxide gas for the controlled delivery of a liquid from a container, comprising:

providing a first and a second chemical, said first and second chemicals being reactive to generate carbon dioxide gas upon contact therebetween at a substantially constant rate, said chemicals being initially separated from one another;

allowing said first and second chemicals to come into contact and react to generate the gas; and communicating said gas to means operative to drive the liquid from the container, wherein, the gas generating reaction is continued for a sufficient length of time to deliver the liquid from the container and the liquid is driven from the container at a substantially constant flow rate.

3. A method to generate carbon dioxide gas for the controlled delivery of a liquid from a container, comprising:

providing an alkali metal carbonate formed into a tablet and a liquid chemical that is reactive with the carbonate to generate carbon dioxide gas, said chemicals being initially separated from one another, and wherein said tablet is at least partially coated with a barrier that is at least partially insoluble in the liquid chemical;

allowing said first and second chemicals to come into contact and react to generate the gas at a substantially constant rate; and communicating said gas to means operative to drive the liquid from the container at a substantially constant flow rate.

4. A method to generate carbon dioxide gas for the controlled delivery of a liquid from a container, comprising:

providing a first and a second chemical, said first and second chemicals being reactive to generate a gas upon contact therebetween, said chemicals being initially separated from one another;

allowing said first and second chemicals to come into contact and react to generate a gas such that upon attainment of the predetermined pressure within the first container, the container is maintained at said predetermined pressure through pressure maintenance means; and communicating said gas to means operative to drive a liquid from said container at a substantially constant flow rate.

5. The method of claim 4, wherein said pressure maintenance means is a pressure relief valve in fluid communication with said container.

6. The method of claim 4, further comprising controlling the reaction rate between said first and second chemicals by admixing au least one of said chemicals with a rate limiting amount of a rate controlling moiety.

7. The method of claim 4, wherein said second chemical is a liquid and said first chemical is a tablet at least partially coated with a barrier that is at least partially insoluble in the liquid chemical, and said method further comprises controlling the reaction rate between said first and second chemicals by the amount of barrier coated onto said tablet.

* * * * *

UNITED STATES PATENT AND TRADEMARK OFFICE
CERTIFICATE OF CORRECTION

PATENT NO. : 5,588,556
DATED : December 31, 1996
INVENTOR(S) : Gregory E. Sancoff, Mark C. Doyle, and Frederic P. Field It is certified that error appears in the above-indentified patent and that said Letters Patent is hereby corrected as shown below:

On the title page, item [54] and Col. 1, lines 1 and 2

In the title, please amend the title to read as follows: GAS DELIVERY APPARATUS AND COMPOSITIONS FOR INFUSION.

Signed and Sealed this

Sixth Day of May, 1997

Attest:

BRUCE LEHMAN

*Attesting Officer*          *Commissioner of Patents and Trademarks*